(12) United States Patent  (10) Patent No.: US 7,008,788 B2
Schremp et al.  (45) Date of Patent: Mar. 7, 2006

(54) CONTAINERS FOR SUPPORTS COMPRISING BIOPOLYMERS

(75) Inventors: Donald J. Schremp, San Jose, CA (US); Richard O. Hilson, Sunnyvale, CA (US); Edward P. Donlon, San Jose, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/919,062

(22) Filed: Jul. 30, 2001

(65) Prior Publication Data

US 2003/0022176 A1  Jan. 30, 2003

(51) Int. Cl.
 *C12M 3/00* (2006.01)
(52) U.S. Cl. .................. 435/287.1; 422/102; 422/104; 435/287.2; 435/287.9; 435/288.2; 435/6; 436/528; 436/532; 436/809; 436/823
(58) Field of Classification Search ............. 435/287.1, 435/287.2, 287.9, 288.2–288.5, 6; 436/518, 436/524, 528, 809, 823, 532; 422/102, 104; 141/100, 231, 250, 285; 215/6, 14, 200, 215/370, 379; 220/560, 560.01, 592.01, 220/4.01, 23.2, 495.01, 23.83, 23.88, 500–502, 220/505–507, 523, 529, 553; 222/92, 129, 222/173, 424.5
See application file for complete search history.

(56) References Cited

U.S. PATENT DOCUMENTS 4,596,723 A * 6/1986 Kaufman et al. ........... 427/336
4,701,754 A * 10/1987 Provonchee ........... 340/815.45
4,828,386 A * 5/1989 Matkovich et al. ......... 356/246
4,844,966 A * 7/1989 Calenoff et al. ........... 435/7.92
4,919,894 A * 4/1990 Daniel ....................... 264/45.9
4,999,163 A * 3/1991 Lennon et al. ................ 422/58
5,096,809 A * 3/1992 Chen et al. ................... 435/7.9
5,595,707 A   1/1997 Copeland et al. ............. 422/64
5,650,327 A   7/1997 Copeland et al. ............. 436/46

(Continued)

FOREIGN PATENT DOCUMENTS

GB  2 197 720 A  *  5/1988

(Continued)

*Primary Examiner*—Christopher L. Chin (57) ABSTRACT

Devices and methods are disclosed for containing and processing samples on the surface of supports. Biopolymer features are attached to the surfaces of the supports. A device in accordance with the invention comprises a housing and a support confined by the housing. The housing comprises a well having walls and at least one wall extending from the edge of the well. The height of the walls of the well is at least great enough, and the design of the at least one wall is such, that liquid contained in the well is not drawn out of the well to any substantial degree by surface tension or small movements or small mechanical vibrations. In one embodiment, the at least one wall is designed such that corners thereof are curved or are distant from the edge of the well to substantially eliminate wicking of liquid from the well. Also disclosed are methods for mixing materials on the surface of a support. A sample is incubated with the surface of the support of the aforementioned device. The sample is removed from the surface, a residual amount of the sample remaining on the surface. The surface is contacted with a wash solution. A stream of gas is directed at the surface of the support. The pressure of the stream and the angle of the stream create a vortex on the surface sufficient to mix the sample and the wash solution. The wash solution is then removed from the surface. Also disclosed are methods for conducting binding reactions using the devices of the invention.

31 Claims, 4 Drawing Sheets

U.S. PATENT DOCUMENTS

| | | | |
|---|---|---|---|
| 5,910,287 A * | 6/1999 | Cassin et al. | 422/102 |
| 6,083,763 A * | 7/2000 | Balch | 436/518 |
| 6,093,574 A | 7/2000 | Druyor-Sanchez et al. | 436/180 |
| 6,238,910 B1 | 5/2001 | Custance et al. | 435/287.2 |
| 6,423,948 B1 * | 7/2002 | Kwasnoski et al. | 219/428 |

FOREIGN PATENT DOCUMENTS

| | |
|---|---|
| WO | WO 94/08759 A1 * 4/1994 |

* cited by examiner

CONTAINERS FOR SUPPORTS COMPRISING BIOPOLYMERS

BACKGROUND OF THE INVENTION

This invention relates to devices for housing supports that comprise biological material on their surfaces and methods of using the devices to process the biological material. More particularly, the present invention relates to packages for slides that have biopolymers on their surfaces. The biopolymers on the surfaces may be subjected to various processing steps such as, e.g., binding reactions, washing, drying, and the like.

Determining the nucleotide sequences and expression levels of nucleic acids (DNA and RNA) is critical to understanding the function and control of genes and their relationship, for example, to disease discovery and disease management. Analysis of genetic information plays a crucial role in biological experimentation. This has become especially true with regard to studies directed at understanding the fundamental genetic and environmental factors associated with disease and the effects of potential therapeutic agents on the cell. Such a determination permits the early detection of infectious organisms such as bacteria, viruses, etc.; genetic diseases such as sickle cell anemia; and various cancers. This paradigm shift has lead to an increasing need within the life science industries for more sensitive, more accurate and higher-throughput technologies for performing analysis on genetic material obtained from a variety of biological sources.

Unique or polymorphic nucleotide sequences in a polynucleotide can be detected by hybridization with an oligonucleotide probe. Hybridization is based on complementary base pairing. When complementary single stranded nucleic acids are incubated together, the complementary base sequences pair to form double stranded hybrid molecules. These techniques rely upon the inherent ability of nucleic acids to form duplexes via hydrogen bonding according to Watson-Crick base-pairing rules. The ability of single stranded deoxyribonucleic acid (ssDNA) or ribonucleic acid (RNA) to form a hydrogen bonded structure with a complementary nucleic acid sequence has been employed as an analytical tool in molecular biology research. An oligonucleotide probe employed in the detection is selected with a nucleotide sequence complementary, usually exactly complementary, to the nucleotide sequence in the target nucleic acid. Following hybridization of the probe with the target nucleic acid, any oligonucleotide probe/nucleic acid hybrids that have formed are typically separated from unhybridized probe. The amount of oligonucleotide probe in either of the two separated media is then tested to provide a qualitative or quantitative measurement of the amount of target nucleic acid originally present. In surface-bound DNA arrays, this separation is typically accomplished by washing the unbound and non-specifically bound material away from the array surface. The resulting wash protocol is normally optimized to the specific requirements of the assay, the probe type, the surface selected and other considerations. The surface is then scanned for the presence of the target.

Direct detection of labeled target nucleic acid hybridized to surface-bound polynucleotide probes is particularly advantageous if the surface contains a mosaic of different probes that are individually localized to discrete, known areas of the surface. Such ordered arrays containing a large number of oligonucleotide probes have been developed as tools for high throughput analyses of genotype and gene expression. Oligonucleotides synthesized on a solid support recognize uniquely complementary nucleic acids by hybridization, and arrays can be designed to define specific target sequences, analyze gene expression patterns or identify specific allelic variations. The arrays may be microarrays created by in-situ synthesis or oligonucleotide deposition. Microarrays created by complementary DNA (cDNA) deposition are used to analyze gene expression patterns and perform genome scanning. Protein arrays are very useful for determining the presence and quantity of specific proteins in a cell or tissue. These arrays may have either proteins or aptamers bound to the surface. Due to the large number of genes in the human genome and other mammals and plants and the large number of proteins created, it is desirable to automate this hybridization process on microarrays.

In one approach, cell matter is lysed, to release its DNA, mRNA or protein which are then separated out by electrophoresis or other means and amplified, if necessary and then tagged with a fluorescent or other label. The resulting mix is exposed to an array of oligonucleotide, cDNA, aptamer or protein probes, whereupon selective binding to matching probe sites takes place. The array is then washed and interrogated to determine the extent of hybridization reactions. In one approach the array is imaged so as to reveal for analysis and interpretation the sites where binding has occurred.

Biological assays involving fluorescently labeled molecules or scattering structures to detect, quantify or identify target chemical species bound to surfaces often use optical detection and imaging systems. Arrays of different chemical probe species provide methods of highly parallel detection, and hence improved speed and efficiency, in assays. These arrays are, for example, DNA arrays and protein matrix arrays, which need to be scanned to measure the number densities of labeled molecules and hence the concentration of target or probe molecules in solution. This sensing process often is accomplished by means of a fluorescence imaging system. Chemiluminescence and radioisotopes are alternative methods commonly employed.

As mentioned above, usually a mosaic of different probes are individually localized to discrete, known areas of a surface of a support. The support may be utilized and analyzed directly or the support may be part of a package, which houses the support. For example, hybridization arrays may be part of a self-contained package. After a hybridization process occurs on the surface of the support, the surface must be washed to remove the unbound and non-specifically bound sample. In a self-contained microarray package, for example, the test sample in the package needs to be washed in order for the features of the microarray to stand out during the detection process such as a scanning process. During the washing process, it is important for the washing protocol be followed precisely in order to remove any excess sample from the actual surface without damaging or destroying the microarray on the surface of the support or causing the hybridized material to melt off the array, thus losing all the signal obtained during the hybridization process.

Previously, hybridizing reactions in DNA microarrays has been done either 1) in a small sealed volume, 2) under a coverslip on a microscope slide or 3) with a larger sample volume in a plastic bag. With the sealed volume solutions the enclosed volume is designed to accommodate the desired sample size and is filled with sample during the hybridization. Because of the very small volumes used, the fluid inside the sealed package experiences large capillary forces making mixing of the fluid difficult. Additional difficulties arise with this technique when sample injection and removal are automated. The coverslip method is not conducive to automation and makes mixing of materials difficult or nearly impossible. The coverslip may not rest parallel to the slide surface, affecting the amount of sample to which each area of the array is exposed. This can result in varying levels of signal. The plastic bag method requires larger sample volumes and is not conducive to automation.

SUMMARY OF THE INVENTION

One embodiment of the present invention is a device comprising a housing and a support confined by the housing. The housing comprises a well having walls and at least one wall extending from an area adjacent the edge of the well. The height of the walls of the well is at least great enough, and the design of the at least one wall is such, that liquid contained in the well is not drawn out of the well to any substantial degree by surface tension or small movements or small mechanical vibrations. In one embodiment, the at least one wall is designed such that corners thereof are curved or are distant from the edge of the well to substantially eliminate wicking of liquid from the well.

Another embodiment of the present invention is a method for mixing materials on the surface of a support. At least one reagent is placed on the surface of the support of the aforementioned device. The surface has at least a residual amount of a sample thereon. A stream of gas is directed at the surface of the support. The pressure and an angle of the stream is such as to create a vortex on the surface sufficient to mix the sample and the at least one reagent.

Another embodiment of the present invention is a method for carrying out a binding reaction. A sample is incubated with the surface of the support of the aforementioned device. The sample is removed from the surface, a residual amount of the sample remaining on the surface. The surface is contacted with a wash solution. A stream of gas is directed at the surface of the support. The pressure of the stream and the angle of the stream create a vortex on the surface sufficient to mix the sample and the wash solution. The wash solution is then removed from the surface.

Another embodiment of the present invention is a method for detecting the presence of a target polynucleotide in a sample. A sample suspected of containing a target polynucleotide is incubated with the surface of the support of the aforementioned device. The sample is removed from the surface wherein a residual amount of the sample remains on the surface. The surface is contacted with a wash solution. A stream of gas is directed at the surface of the support. The pressure of the stream and the angle of the stream create a vortex on the surface sufficient to mix the sample and the wash solution. The wash solution is removed from the surface, and the surface is examined for the presence of a binding reaction between the polynucleotides thereon and the target polynucleotide. The presence of a binding reaction indicates the presence of the target polynucleotide in the sample.

Another embodiment of the present invention is a method for mixing materials on the surface of a support. In the method at least one reagent is placed on the surface of the support. The surface has at least a residual amount of a sample thereon. No evaporation layer is present over the reagent on the surface of the support. A stream of gas is directed at the surface of the support. The pressure of the stream and the angle of the stream create a vortex on the surface sufficient to mix the sample and the reagent.

Another embodiment of the present invention is a method for mixing materials on the surface of a support. At least one reagent is placed on the surface of the support. The surface has at least a residual amount of a sample remaining on the surface. A stream of gas is directed at or between the centerline and the edge of the surface of the support. The pressure of the stream and the angle of the stream create a vortex on the surface sufficient to mix the sample and the reagent.

Another embodiment of the present invention is an apparatus for elevating the temperature adjacent a support comprising biopolymers bound to a surface of the support. The apparatus comprises a housing, a chamber within the housing and at least one heating element for elevating the temperature adjacent the support. The chamber is adapted to receive the coverless container. In one embodiment the housing may comprise a top portion and a bottom portion. The top portion comprises a top wall and a downwardly depending wall. The inner surface of the top wall is adapted to sealing engage a top portion of the coverless container. The bottom portion is adapted to engage the downwardly depending wall of the top portion such that the chamber is formed by the engagement of the top portion and the bottom portion. One or both of the top portion and the bottom portion may comprise a heating element.

Another embodiment of the present invention is a method for heating a liquid on a support. The method comprises creating a temperature gradient on opposite sides of the support. The temperature gradient is sufficient to substantially reduce condensation of the liquid during the heating. The support may be housed in a coverless container, which may be in the chamber of a housing where two heating elements are positioned on opposing sides of the support.

DETAILED DESCRIPTION OF THE INVENTION

In the present invention a volume of a fluid sample is contained in a well created by walls around the perimeter of a support such as a glass slide. The well is part of a housing for the support. At least one wall extends from the edge of the well and ultimately to the top of the housing. We have found that wicking or other movement of the liquid from the well may be controlled by the height of the walls of the well and/or by the avoidance of sharp corners or angles adjacent the edge of the well. In this regard at least one wall extending from the edge of the well may be sloped from the edge of the well or any corners formed by such wall as it proceeds to the top of the housing may be curved to avoiding wicking of fluid sample from the well. In the latter approach a portion or all of the at least one wall may be sloped from the edge of the well to the top of the housing or may be sloped from an area adjacent the edge of the well to the top of the housing. Accordingly, the wall may include a horizontal portion proceeding from the edge of the well in the form a ledge and may further include a sloped portion extending from the ledge to the top of the housing. The sloped portion in this approach usually has a varying slope as opposed to a constant slope as discussed herein below. In another approach involving a ledge, any angled corners are placed at a distance that is remote to the edge of the well so as to substantially reduce or eliminate wicking of liquid sample in the well.

The sample in the well may or may not be covered. If the well is covered, enough air volume above the sample is provided to prevent the sample from touching the cover. Mixing of materials on the surface of the support may be accomplished by mechanical motion or by impinging a gas stream on the surface of the support.

In one embodiment a device in accordance with the present invention comprises a housing and a support confined by the housing. Normally, the support is confined below a well, which is part of the housing. The well comprises side walls that extend away from the support, which represents a bottom wall of the well and of the housing. Usually, the well is formed by a wall or walls that extend vertically away from the support. The height of the walls is usually at least great enough so that liquid contained in the well is not drawn out of the well to any significant degree by surface tension or small mechanical motion or vibration. In other words the height should be great enough to avoid significant wicking of liquid contained within the well. Thus, the height of the well should be great enough that no more than about 25% of liquid is drawn out of the well, usually, no more than about 5%, and preferably, no more than about 1%.

The height of the walls of the well is dependent in part on the dimensions of the support, which usually has a shape that is square, rectangular, circular, oval, parabolic or the like. The dimensions of a square support are usually about 0.5 inches (about 12.7 mm) to about 1.5 inches (about 38.10 mm) by about 0.5 inches (about 12.7 mm) to about 1.5 inches (about 38.10 mm), more usually, about 1 inch by about 1 inch (about 25.4 by about 25.4 mm). The dimensions of a rectangular support are usually about 0.5 inches (about 12.7 mm) to about 1.5 inches (about 38.10 mm) by about 2.0 inches (about 50.8 mm) to about 4.0 inches (about 101.6 mm), more usually, about 1 inch by about 3 inches (about 25.4 by about 76.20 mm), which approximates the standard microscope slide. Generally, the thickness of the support is about 0.030 to about 0.05 inches (about 0.75 to about 1.27 mm), usually, about 0.039 to about 0.0453 inches (about 1.00 to about 1.15 mm). In general, the shape of the well follows the shape of the support. Thus, with a circular or oval support, the well may be circular or oval in which case the well is formed by a single wall that encircles the support. Usually, the height of the well is at least about 0.005 inches, usually, at least about 0.010 inches, more usually, at least about 0.015 inches.

The maximum height of the well is dependent on several factors. One such factor is the ease of processing of samples in the well. The lower the height of the well, the easier is the washing and drying of the surface. Furthermore, the lower the height of the well, the lower the meniscus that forms between the nominal level of the liquid in the well and the walls of the well. A higher meniscus can significantly reduce the amount of liquid available over the surface of the support. Lower well height reduces the volume of liquid in the meniscus allowing a larger percentage of the liquid to remain over the surface of the support. In addition, the lower the meniscus, the less the amount of liquid that will be trapped in the well and the easier the well may be flushed with wash solutions and the like. Also, a lower meniscus presents a smaller barrier and the removal of liquid from the surface of the support may be carried out in a much more facile manner with, for example, an air knife. The well height should be high enough to prevent liquid from overflowing the well. This latter situation may also be controlled by the amount of liquid applied to the well. In general, it is desirable to use as little volume of liquid as possible to conserve sample and reagents. Usually, the volume of liquid is about 50 to about 1500 microliters, more usually, about 75 to about 300 microliters, preferably about 200 microliters. In general, the maximum height of the well is no greater than about 0.050 inches, usually, no greater than about 0.015 inches. It should be noted that, as discussed hereinbelow, the sloping of the walls of the housing in the area adjacent the well significantly reduces the amount of liquid that may be drawn out of the well by surface tension.

The housing may be fabricated from plastic, metal, ceramic, glass and the like. The material from which the housing is made must be substantially inert to the liquids that are contacted with the housing. The housing may be fabricated by methods known in the art such as, for example, machining, casting, molding, injection molding, compression molding, or thixotropic molding.

The support to which a plurality of biopolymers is attached is usually a porous or non-porous water insoluble material. The support can have any one of a number of shapes, but is usually a strip, plate, disk, or the like. The support can be hydrophilic or capable of being rendered hydrophilic or the support may be hydrophobic, or capable of being rendered hydrophobic. The support is usually glass such as flat glass whose surface has been chemically activated to support binding or synthesis of biopolymers such as polynucleotides, glass available as Bioglass and the like. However, the support may be made from materials such as inorganic powders, e.g., silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; ceramics, metals, and the like. Preferably, the support used in a packaged array is glass, plastic or some other non-porous material. Binding of substances such as oligonucleotides to a support or surface may be accomplished by well-known techniques, commonly available in the literature. See, for example, A. C. Pease, et al., *Proc. Nat. Acad. Sci. USA*, 91:5022–5026 (1994).

The support is generally affixed to the bottom of the housing to form the bottom of the well. In that regard the bottom of the housing comprises an opening surrounded by a recess into which the support is secured. The support is oriented such that the surface of the support that comprises biopolymers faces inward into the housing and the well. When the support is in place, the well is complete with side walls and bottom wall. The support is affixed into the recess generally by securing the support to a lip around the perimeter of the recess. The support is secured by appropriate means such as adhesives, e.g., epoxy, double-sided adhesive tape and the like, welding, molding in place and so forth. It should be apparent that the support is secured to the bottom of the housing with a liquid tight seal so that liquid, when placed in the well, will not leak from the well. The external surface of the support may be flush with the bottom external surface of the housing or it may protrude beyond the external bottom surface of the housing. In a sense the support may be mounted into a framed opening in the bottom portion of the housing. Although the above description has focused on a separate support mounted in the bottom of the housing, it is within the purview of the present invention that a bottom wall of the housing comprises a portion that comprises attached biopolymers. In other words, in this embodiment the support is integral with the bottom wall of the housing.

The housing comprises at least one wall extending from the edge of the well. The number of walls depends on the configuration of the housing above the well. For example, the housing may comprise a single, circular or oval wall or the like extending from the well to the top portion of the housing. On the other hand, there may be two to four or more walls, each extending from an area adjacent a respective wall of the well.

The present devices are designed to reduce or eliminate wicking of liquid out of the well. To this end we have found that sharp angular corners near the top edge of the well contribute to such wicking. In accordance with one aspect of the present invention, the walls of the device are sloped to reduce the wicking produced by such corners. At least a portion of at least one wall of the housing is sloped in an area thereof adjacent the well. The sloped portion of the wall may constitute substantially the entire wall or a portion of the wall that is about 60 to about 95%, usually about 80 to about 90% of the length of the wall. The portion of the wall that is sloped is usually sloped at an angle of about 15 to about 60 degrees, more usually, about 30 to about 55 degrees, from the horizontal.

In general, the walls of the housing are sloped to an extent sufficient to substantially reduce or eliminate wicking of liquid contained in the well. Where the housing comprises four walls, at least one of the walls has at least a portion thereof that is sloped, usually, at least two of the walls have at least a portion that is sloped, and all four walls may have a portion that is sloped. The sloped portion of the walls may be sloped to the same degree or the sloping of the walls may differ as long as the above considerations are observed.

In one aspect of the sloping of the walls, any corners that are close enough to the edge of the wall to cause wicking of liquid in the well to any significant extent are curved to an extent necessary to reduce or eliminate wicking. To achieve the necessary curvature in this embodiment, the slope is continuously changing rather than substantially constant resulting in a straight line. The curve formed in the former situation is usually concave. The curve removes the sharpness or angularity of the corners that would otherwise be present when the wall has one portion that is substantially horizontal, thereby forming a ledge portion, and one portion that extends in a vertical manner to the top of the housing. The corners, therefore, may be viewed as radiused, or not angled, because of the curved slope. In many embodiments, the radius of such curvature is about 1/8 to about 1/32 inch, and in some embodiments the radius is about 1/16 inch.

Figure 15:
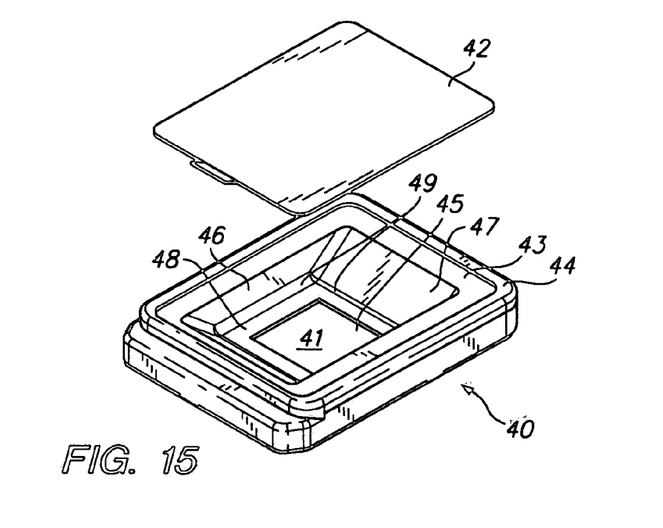
FIG. 15 is a diagrammatic sketch showing a device of the invention with a flexible peel-back lid cover.

Referring to FIG. 15, device 40 is depicted and comprises support 41 affixed to the bottom of device 40 in a manner as discussed above. Support 41 forms a bottom wall of well 45, which comprises walls 46 and 47. Device 40 further comprises ledge 48 as well as two sets of two walls each for a total of four walls. Walls 46 and 47 are sloped from radius 49 of ledge 48 to top portion 43 of housing 44 of device 40. Surface 43 is below the top surface 44 in order for item 42 to be flush with surface 44.

In another approach, corners are designed in such as way as to be out of proximity of the edge of the well. In this way, the corner is far enough removed from the edge of the well that it cannot cause wicking of fluid out of the well. The distance of removal from the edge, or in other words the width of the ledge, in this embodiment is dependent on the extent of the angle of the corners. In general, the closer the angle to 90 degrees, the higher is the degree of wicking ability. As the angle decreases towards zero degrees, the ability to wick liquids from the well decreases. Accordingly, the closer the angle to 90 degrees, the greater the distance of removal of the corner from the edge of the well. In this approach, the corners are usually about 0.1 inch to about 1 inch, more usually, about 0.2 inches to about 0.5 inches, from the edge of the well.

The wall(s) of the housing may extend from an edge of the top of the well to a top portion of the housing. Alternatively, the wall(s) of the housing may extend from a ledge, which extends from an edge of the top of the well to the wall(s). Generally, the ledge is substantially horizontal and substantially parallel with the surface of the support at the bottom of the well. The shape of the ledge may be rectangular, circular, oval, parabolic and the like, preferably, rectangular or circular. The dimensions of the ledge are dependent on a number of factors such as the avoidance of wicking of liquid in the well, the size of the support, the size of the housing, and so forth. Usually, the distance between the edge of the well closest to the wall(s) and the wall(s) is at least about 0.050 inches, more usually, at least about 0.100 inches. The maximum distance between the closest edge of the well and the wall(s) of the housing is usually no more than about 1.00 inches, more usually, no more than about 0.300 inches.

To further reduce wicking of liquid in the well, the surface of the ledge may comprise one or more features that reduce or prevent wicking by reducing the surface energy of the ledge. Such features include, for example, polishing the surface, and the like. The surface finish of the polished surface is usually in the range of about 4 to about 16 microinches, usually about 4 to about 8 microinches.

There are many variations of the device of the invention. Some of these variations are set forth below by way of illustration and not limitation. In one embodiment at least one wall has at least a portion that is sloped, and may be fully sloped, from the edge of the well to a top portion of the housing. Only one wall is present in devices where the wall is circular. However, the device may have two to four or more walls extending from the edge of the well to the top of the housing. At least one of the walls has at least a portion that is sloped, and may be fully sloped, from the edge of the well to the top of the housing. Usually, at least two of the walls are sloped either fully or partially. In one embodiment, all four of the walls are sloped either fully or partially. As discussed above, a ledge may extend from an edge of the well to the sloping portion of the wall(s). In one embodiment the wall(s) comprises a partially sloped portion in an area adjacent the ledge and a vertical portion extending from the partially sloped portion to a top portion of the device. In another embodiment the wall is a circular wall extending from a ledge adjacent the edge of the well to the top portion of the device. In other embodiments, more than one wall is present, as discussed in the embodiments above, wherein at least one of the walls has at least a portion that is sloped and may be fully sloped from the ledge, or an area adjacent thereto. For example, the device may comprise at least two walls that are fully sloped from a ledge adjacent the edge of the well to the top portion of the device. In another variation the device may comprise two opposing walls that are fully sloped from a ledge adjacent the edge of the well to the top portion of the device and two opposing walls extending vertically from the ledge to the top portion. In another variation the device comprises four walls that are fully sloped from a ledge adjacent the edge of the well to the top portion of the device.

Usually, the support in the housing is mounted such that the front side of the support, i.e., the side upon which biopolymers are attached, is facing into the well so that the bottom wall of the well comprises the surface with the biopolymers thereon. In this configuration sample and reagents added to the well are in contact with biopolymers on the surface of the support.

An advantage of the present devices is that a cover or lid is not required. In that sense the devices are coverless. However, there may be some instances where a cover is employed such as, for example, to avoid significant loss by evaporation during heating, to protect the biopolymers during shipping, storage, etc. For example, a cover may be desirable during reactions that are carried out at least in part at elevated temperatures. For example, hybridization reactions sometimes require elevated temperatures. In the event that a cover is desired for a certain operation, it is normally only used during such operation. The cover is usually one that can be put into placed and/or removed with relative ease. The cover may be, for example, a flexible, pliable film such as plastic or metal-foil film, which is attached to, and covers a top portion of, the housing of the present device. In this approach the cover closes off a large enclosed chamber. Alternatively, the cover may be designed to cover only the well of the present device, which thus covers only a relatively smaller chamber, i.e., the well of the device.

The removal of the cover is dependent on the nature of the cover. The cover may be affixed to the housing of the device by interference, friction fit, heat staking, or adhesive to enable the cover to be removed. On the other hand, the cover may be such that it may be removed by peeling off the cover. In this embodiment the cover typically will be a malleable material such as, for example, foil, e.g., a metal foil such as aluminum foil, thin plastic, a plastic-metal laminate, e.g., metallized mylar, a deformable rubber dam or septum, and the like. In another approach the cover may be one that comprises a lid that comprises an O-ring on one side and the cover is secured by means of pressure exerted on the back side of the lid, i.e., the side opposite the O-ring.

In one specific embodiment, FIG. 15, the cover is a re-sealable, flexible, pliable film 42 such as plastic or metal-foil film, which is attached to, and covers one face of, the device 40. This lid closes off large chamber 41. Sample solution is introduced into this enclosed chamber by peeling back the pliable film cover 42 and introducing fluid directly into chamber 41. The film is re-sealed and the support housing is incubated to bind labeled molecules within the sample solution to molecules bound to the surface of the support. After binding, the film can be peeled away from the surface of the support to facilitate removal of the sample solution from the surface of the support in accordance with the present invention. The film is peeled back and discarded in a manner similar to that on, for example, a dairy product container.

The apparatus and methods of the present invention are particularly useful in the area of chemical processing of arrays of biopolymers. The present invention allows automation of wet chemical processing steps that typically occur in arrays of biopolymers. Currently, the wet chemical processing is conventionally performed by human laboratory technicians. Human involvement introduces variability and errors from fatigue and the like into the processing protocol. The apparatus and methods of the present invention circumvent fatigue and can operate continuously for long periods of time without degradation in uniformity and the like. The present invention reduces or eliminates process variability and minimizes errors since its operation is mechanically consistent and the actions of the mechanism are algorithmically controlled. The invention provides greater uniformity in executing chemical processing steps often associated with arrays of biopolymers.

A biopolymer is a polymer of one or more types of repeating units relating to biology. Biopolymers are typically found in biological systems (although they may be made synthetically) and particularly include peptides or polynucleotides, as well as such compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions.

An array includes any one, two or three dimensional arrangement of addressable regions bearing a particular biopolymer such as polynucleotides, associated with that region. An array is addressable in that it has multiple regions of different moieties, for example, different polynucleotide sequences, such that a region or feature or spot of the array at a particular predetermined location or address on the array can detect a particular target molecule or class of target molecules although a feature may incidentally detect non-target molecules of that feature.

The apparatus and methods of the present invention are particularly useful in the area of chemical processing of oligonucleotide and polynucleotide arrays for determinations of polynucleotides. In the field of bioscience, arrays of oligonucleotide or polynucleotide probes, fabricated or deposited on a surface of a support, are used to identify DNA sequences in cell matter. Additionally, they are used to detect and quantify gene expression by detecting mRNA. The arrays generally involve a surface containing a mosaic of different oligonucleotides or sample nucleic acid sequences or polynucleotides that are individually localized to discrete, known areas of the surface. In one approach, multiple identical arrays across a complete front surface of a single substrate or support are used. However, the arrays produced on a given substrate need not be identical and some or all could be different. Each array may contain multiple spots or features and each array may be separated by spaces. Each feature, or element, within the molecular array is defined to be a small, regularly shaped region of the surface of the substrate. The features are arranged in a regular pattern. Each feature within the molecular array may contain a different molecular species, and the molecular species within a given feature may differ from the molecular species within the remaining features of the molecular array. A typical array may contain from about 100 to about 100,000 or more features. All of the features may be different, or some or all may be the same. Each feature may carry a predetermined polynucleotide having a particular sequence or a predetermined mixture of polynucleotides. While arrays may be separated from one another by spaces, and the features may be separated from one another by spaces, such spaces in either instance are not essential.

Ordered arrays containing a large number of oligonucleotides and polynucleotides have been developed as tools for high throughput analyses of genotype and gene expression. Oligonucleotides synthesized on a solid support recognize uniquely complementary nucleic acids by hybridization, and arrays can be designed to define specific target sequences, analyze gene expression patterns or identify specific allelic variations. The arrays may be used for conducting cell study, for diagnosing disease, identifying gene expression, monitoring drug response, determination of viral load, identifying genetic polymorphisms, analyze gene expression patterns or identify specific allelic variations, and the like.

Oligonucleotide probes are oligonucleotides employed to bind to a portion of a polynucleotide such as another oligonucleotide or a target polynucleotide sequence. Usually, the oligonucleotide probe is comprised of natural nucleotides such as ribonucleotides and deoxyribonucleotides and their derivatives although unnatural nucleotide mimetics such as 2'-modified nucleosides, peptide nucleic acids and oligomeric nucleoside phosphonates are also used. The design, including the length, and the preparation of the oligonucleotide probes are generally dependent upon the sequence to which they bind. Usually, the oligonucleotide probes are at least about 2 nucleotides, preferably, about 5 to about 100 nucleotides, more preferably, about 10 to about 70 nucleotides, and usually, about 20 to about 60 nucleotides, in length.

Polynucleotides are compounds or compositions that are polymeric nucleotides or nucleic acid polymers. The polynucleotide may be a natural compound or a synthetic compound. The polynucleotides include nucleic acids, and fragments thereof, from any source in purified or unpurified form including DNA (dsDNA and ssDNA) and RNA, including tRNA, mRNA, rRNA, mitochondrial DNA and RNA, chloroplast DNA and RNA, DNA/RNA hybrids, or mixtures thereof, genes, chromosomes, plasmids, cosmids, the genomes of biological material such as microorganisms, e.g., bacteria, yeasts, phage, chromosomes, viruses, viroids, molds, fungi, plants, animals, humans, and the like. The polynucleotide can be only a minor fraction of a complex mixture such as a biological sample. Also included are genes, such as hemoglobin gene for sickle-cell anemia, cystic fibrosis gene, oncogenes, cDNA, and the like. The polynucleotide can be obtained from various biological materials by procedures well known in the art. A target polynucleotide sequence is a sequence of nucleotides to be identified, detected or otherwise analyzed, usually existing within a portion or all of a polynucleotide.

A molecular array can be prepared on the surface of a support according to standard molecular array preparation techniques Various ways may be employed to produce an array of polynucleotides on surfaces of supports such as glass, metal, plastic and the like. Such methods are known in the art. One such method is discussed in U.S. Pat. No. 5,744,305 (Fodor, et al.) and involves solid phase chemistry, photolabile protecting groups and photolithography. Binary masking techniques are employed in one embodiment of the above. In another approach ink jet technology may be used to spot polynucleotides and other reagents on a surface as described, for example, in PCT application WO 89/10977. Other methods include those disclosed by Gamble, et al., WO97/44134; Gamble, et al., WO98/10858; Baldeschwieler, et al., WO95/25116; Brown, et al., U.S. Pat. No. 5,807,522; and the like.

Commonly, in polynucleotide detection binding of an oligonucleotide probe to a target polynucleotide sequence is detected by means of a label incorporated into the target. Alternatively, the target polynucleotide sequence may be unlabeled and a second oligonucleotide probe may be labeled. Binding can be detected by separating the bound second oligonucleotide probe or target polynucleotide from the free second oligonucleotide probe or target polynucleotide and detecting the label. In one approach, a sandwich is formed comprised of one oligonucleotide probe, which may be labeled, the target polynucleotide and an oligonucleotide probe that is or can become bound to a surface of a support. Alternatively, binding can be detected by a change in the signal-producing properties of the label upon binding, such as a change in the emission efficiency of a fluorescent or chemiluminescent label. This permits detection to be carried out without a separation step. Finally, binding can be detected by labeling the target polynucleotide, allowing the target polynucleotide to hybridize to a surface-bound oligonucleotide probe, washing away the unbound target polynucleotide and detecting the labeled target polynucleotide that remains. Direct detection of labeled target polynucleotide hybridized to surface-bound oligonucleotide probes is particularly advantageous in the use of ordered arrays.

The signal referred to above may arise from any moiety that may be incorporated into a molecule such as an oligonucleotide probe for the purpose of detection. Often, a label is employed, which may be a member of a signal producing system. The label is capable of being detected directly or indirectly. In general, any reporter molecule that is detectable can be a label. Labels include, for example, (i) reporter molecules that can be detected directly by virtue of generating a signal, (ii) specific binding pair members that may be detected indirectly by subsequent binding to a cognate that contains a reporter molecule, (iii) mass tags detectable by mass spectrometry, (iv) oligonucleotide primers that can provide a template for amplification or ligation and (v) a specific polynucleotide sequence or recognition sequence that can act as a ligand such as for a repressor protein, wherein in the latter two instances the oligonucleotide primer or repressor protein will have, or be capable of having, a reporter molecule and so forth. The reporter molecule can be a catalyst, such as an enzyme, a polynucleotide coding for a catalyst, promoter, dye, fluorescent molecule, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, a mass tag that alters the weight of the molecule to which it is conjugated for mass spectrometry purposes, and the like.

Figure 1:
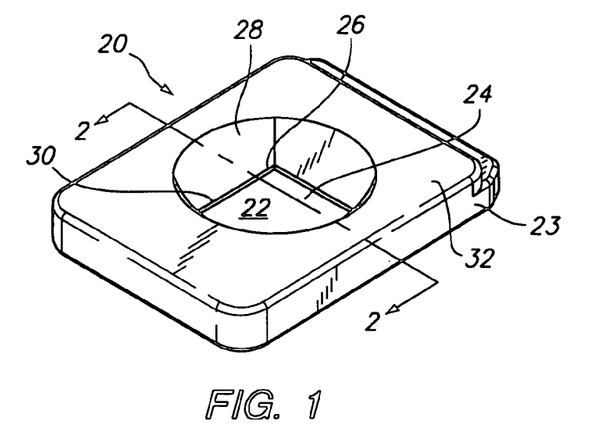
FIG. 1 is a diagrammatic sketch showing in perspective one embodiment of a device in accordance with the present invention.
Figure 2:
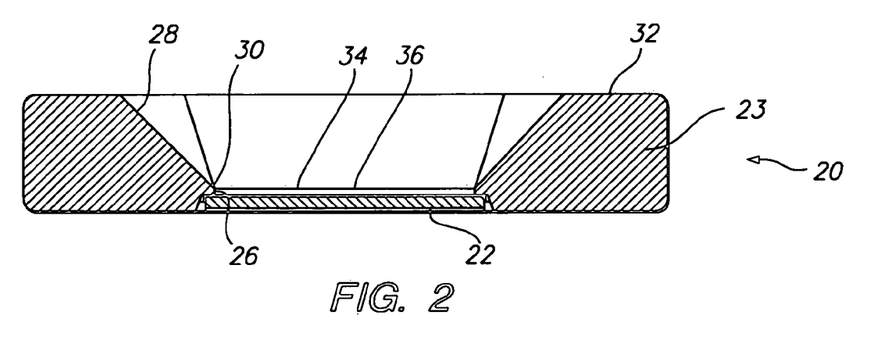
FIG. 2 is a cross-sectional view of the device of FIG. 1 taken along lines 2—2.

Several embodiments of the devices of the invention are described next with reference to the accompanying figures. It should be noted that this description is by way of illustration and not limitation. Other embodiments of the present invention will be apparent to those skilled in the art in light of the disclosure herein. One embodiment of the invention is depicted in FIGS. 1–2. Referring to FIG. 1 device 20 is depicted and comprises support 22 affixed to the bottom of housing 23 of device 20 in a manner as discussed above. Support 22 forms a bottom wall of well 24, which comprises walls 26. Device 20 also comprises a single circular wall 28 that is sloped from edge 30 of well 24 to top portion 32 of housing 23 of device 20. As can be seen, top portion 32 is generally a flat surface extending from wall 28 to the outer edge of housing 23. FIG. 2 is a cross-sectional view of the device of FIG. 1 taken along lines 2—2. Liquid 34 is shown in well 24 of device 20 and has meniscus 36.

Figure 3:
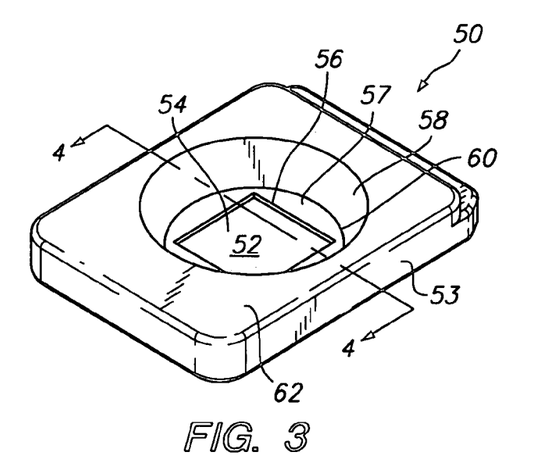
FIG. 3 is a diagrammatic sketch showing in perspective another embodiment of a device in accordance with the present invention.
Figure 4:
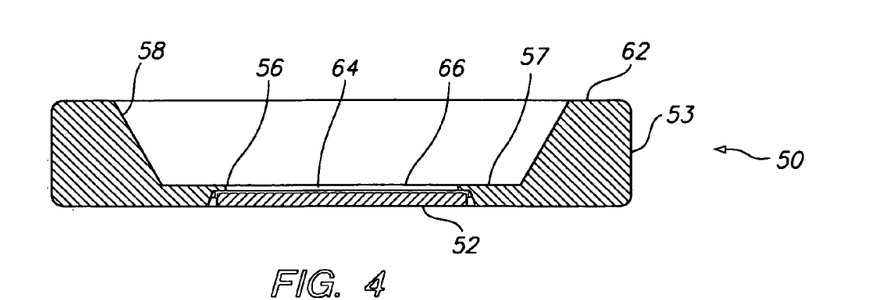
FIG. 4 is a cross-sectional view of the device of FIG. 3 taken along lines 4—4.

Another embodiment of the invention is depicted in FIGS. 3–4. Referring to FIG. 3 device 50 is depicted and comprises support 52 affixed to the bottom of the device in a manner as discussed above. Support 52 forms a bottom wall of well 54, which comprises walls 56. Device 50 further comprises ledge 57 as well as a single circular wall 58 that is sloped from edge 60 of ledge 57 to top portion 62 of housing 53 of device 50. FIG. 4 is a cross-sectional view of the device of FIG. 3 taken along lines 4—4. Liquid 64 is shown in well 54 of device 50 and has meniscus 66.

Figures 5, 6:
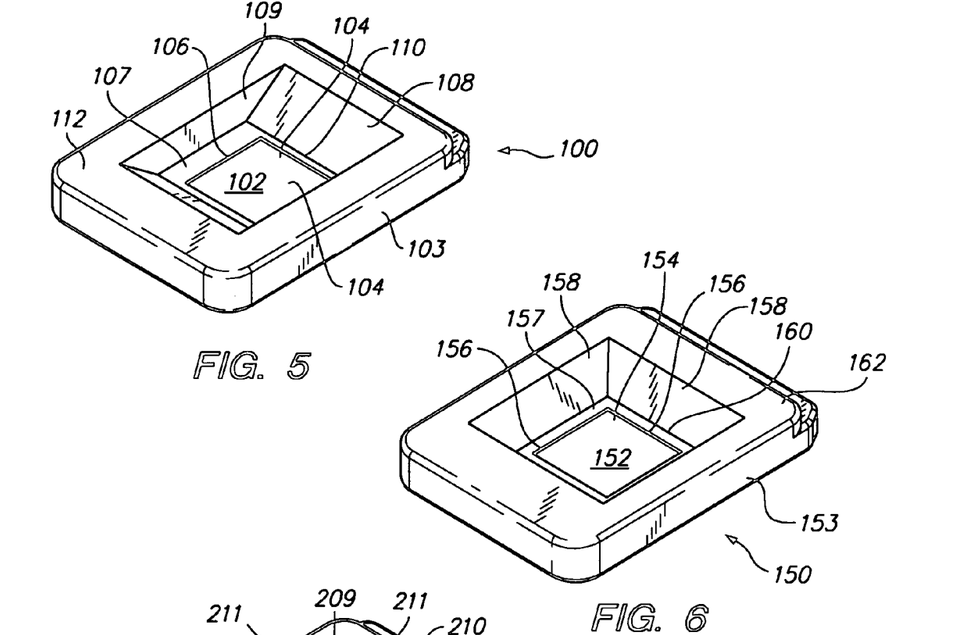
FIG. 5 is a diagrammatic sketch showing in perspective another embodiment of a device in accordance with the present invention.
FIG. 6 is a diagrammatic sketch showing in perspective another embodiment of a device in accordance with the present invention.

Another embodiment of the invention is depicted in FIG. 5. Referring to FIG. 5 device 100 is depicted and comprises support 102 affixed to the bottom of device 100 in a manner as discussed above. Support 102 forms a bottom wall of well 104, which comprises walls 106. Device 100 further comprises ledge 107 as well as two sets of two walls each for a total of four walls. Walls 108 are sloped from edge 110 of ledge 107 to top portion 112 of housing 103 of device 100. Walls 109 extend vertically from edge 110 of ledge 107 to top portion 112 of device 100, that is, walls 109 are substantially straight and have no significant sloping.

Another embodiment of the invention is depicted in FIG. 6. Referring to FIG. 6 device 150 is depicted and comprises support 152 affixed to the bottom of device 150 in a manner as discussed above. Support 152 forms a bottom wall of well 154, which comprises walls 156. Device 150 further comprises ledge 157 as well as four walls 158. Walls 158 are each sloped from edge 160 of ledge 157 to top portion 162 of housing 153 of device 150.

Figure 7:
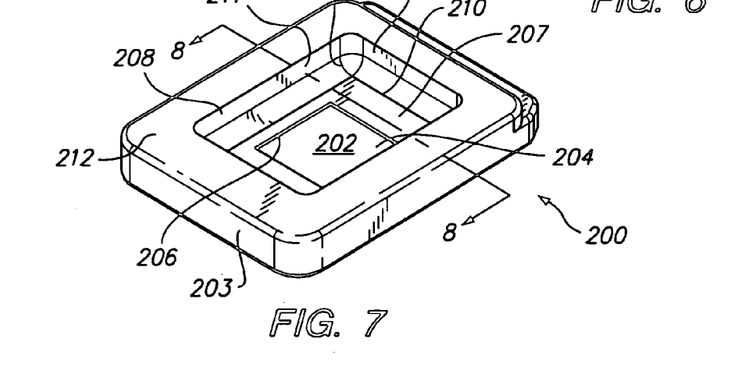
FIG. 7 is a diagrammatic sketch showing in perspective another embodiment of a device in accordance with the present invention.
Figure 8:
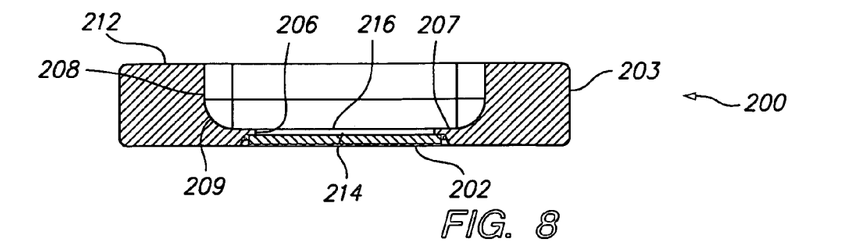
FIG. 8 is a cross-sectional view of the device of FIG. 7 taken along lines 8—8.

Another embodiment of the invention is depicted in FIGS. 7–8. Referring to FIG. 7 device 200 is depicted and comprises support 202 affixed to the bottom of device 200 in a manner as discussed above. Support 202 forms a bottom wall of well 204, which comprises walls 206. Device 200 further comprises ledge 207 as well as four walls 208 that are partially sloped, i.e., comprise sloped portion 209 extending from edge 210 of ledge 207 to a vertical portion 211 of walls 208. Vertical portion 211 extends to top portion 212 of housing 203 of device 200. FIG. 8 is a cross-sectional view of the device of FIG. 7 taken along lines 8—8. Liquid 214 is shown in well 204 of device 200 and has meniscus 216.

Figures 9, 10:
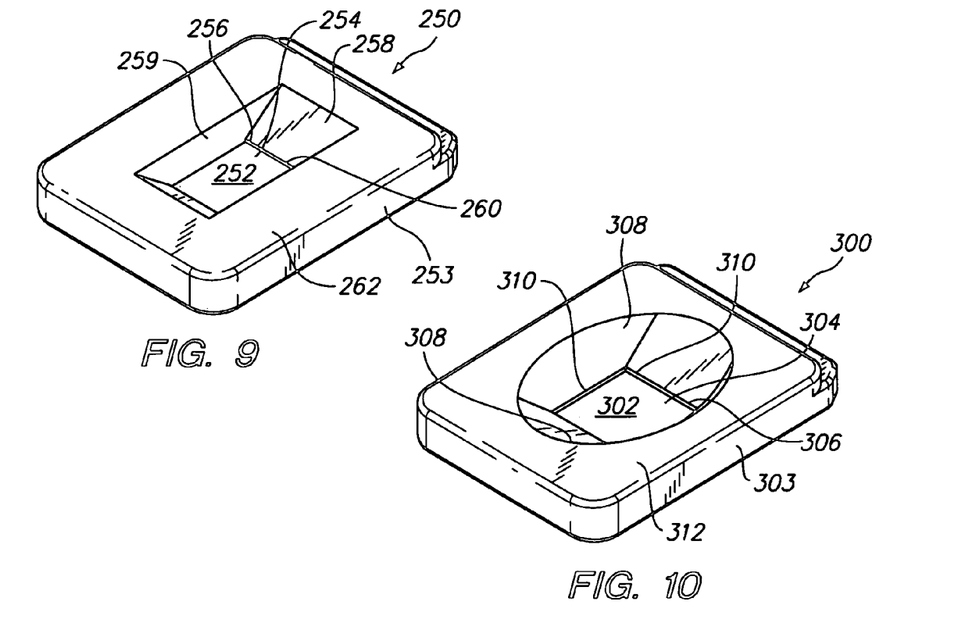
FIG. 9 is a diagrammatic sketch showing in perspective another embodiment of a device in accordance with the present invention.
FIG. 10 is a diagrammatic sketch showing in perspective another embodiment of a device in accordance with the present invention.

Another embodiment of the invention is depicted in FIG. 9. Referring to FIG. 9 device 250 is depicted and comprises support 252 affixed to the bottom of device 250 in a manner as discussed above. Support 252 forms a bottom wall of well 254, which comprises walls 256. Device 250 further comprises two sets of two walls each for a total of four walls. Walls 258 are sloped from edge 260 of well 254 to top portion 262 of device 250. Walls 259 extend vertically from edge 260 of well 254 to top portion 262 of housing 253 of device 250, that is, walls 259 are substantially straight and have no significant sloping.

Another embodiment of the invention is depicted in FIG. 10. Referring to FIG. 10 device 300 is depicted and comprises support 302 affixed to the bottom of device 300 in a manner as discussed above. Support 302 forms a bottom wall of well 304, which comprises walls 306. Device 300 further comprises a single continuous wall 308, which is sloped from edge 310 of well 304 to top portion 312 of housing 303 of device 300. The slope of wall 308 is not constant but rather is continuously changing from edge 310 to top portion 312. The configuration of wall 308 in device 300 is not circular; wall 308 is stadium-like or oval.

The devices of the invention have particular application in the area of binding reactions involving biopolymers such as hybridization reactions involving polynucleotides. One embodiment is described next by way of illustration and not limitation. During the initial portion of a hybridization experiment, a sample solution containing labeled molecules is introduced into the well of a device in accordance with the invention. The sample solution of predetermined volume is introduced into the open well of the present device by, for example, manual pipette, manual syringe, automatic fluid dispensing machine and so forth. The sample solution spreads across the surface of the support, which comprises polynucleotides as a molecular array, by means of capillary action and may be assisted in spreading by means of, for example, pressure exerted by the means of application mentioned above.

Once the sample solution has been distributed across the surface of the molecular array, the sample solution is held in place by gravity and surface tension, which manifests itself in the form of a meniscus in the well of the device as discussed above. Hybridization between molecules in the sample solution and molecules affixed to the inner surface of the support comprising a molecular array on the surface of the support is then allowed to proceed. Following hybridization, buffer solution can be introduced into the device to rinse the sample solution from the surface of the support comprising the molecular array. The volume of the buffer solution is usually greater than the volume of the sample solution, usually being at least about 10 times greater, more usually, at least about 100 times greater. In this regard the buffer solution combines with the sample solution and occupies the larger chamber that is above the well of the present device. The larger chamber is formed by the walls of the device extending to the top of the device.

The buffer solution may be introduced by means of, for example, manual pipette, syringe and needle, delivery and aspiration nozzles of a dispensing apparatus, and the like. The diluted sample solution can be removed from the device by the means involved in its introduction. For example, the solution may be removed by means of a manual syringe and needle, an aspiration nozzle, manual pipette, pump or vacuum action and so forth. Following rinsing, a buffer solution may be left in the chamber of the device in order to maintain the inner surface of the support comprising the molecular array in a hydrated state. The larger volume chamber of the present device greatly facilitates sample solution removal and rinsing of the support and the smaller volume of the well permits the use of relatively small quantities of sample solution to contact the surface of the support. In addition, the ability to place the wash fluid or other fluids in the larger chamber permits washing of the surface of the support in the device itself. The design of the present devices, providing an open top, allows easy access into the larger chamber for introduction and removal of fluids. Inlets and outlets in the form of nozzles and the like may be introduced with relative ease into the large chamber of the device.

As mentioned above, an advantage of the present devices is that they do not necessarily comprise a cover or lid. The open design of the present devices permits easy access to the interior of the device. Accordingly, the open design permits the use of an air knife to remove liquids from the surface of the support. Thus, a washing and removal system can be constructed that does not have components that touch the sample or any part of the surface of the support that the sample touches during reactions. In this way cross-contamination problems that could occur with syringes and needles are minimized by the use of an air knife. Furthermore, washing of the needles and syringes becomes unnecessary. In the use of an air knife, a force sufficient to provide effective removal of liquids from the surface of a support is applied to the surface of the supports within the present devices. The force normally comprises a pressurized gas stream applied by means of, for example, a manual air nozzle, or a air knife nozzle, such as an EXAR Model #110003 "Super Air Knife" and the like. Usually, this process is accomplished at a temperature of about 0° C. to about 60° C., more usually, about 25° C. to about 40° C., more usually, at ambient temperature.

After the support has been contacted with the appropriate reagents and wash solutions, it is usually dried and the surface of the support is examined for the results of any reactions that may have occurred. Any convenient drying device may be employed that is consistent with the nature of materials on the supports. The temperature for drying should be such as not to damage any materials that have reacted with corresponding materials present on the surface of the support. Usually, the supports are dried at a temperature of about 0° C. to about 60° C., more usually, about 25° C. to about 40° C., more usually, at ambient temperature. The drying may be accomplished by, for example, a forced-air or inert gas dryer employing an air-knife configuration, a centrifugal-force spin dryer, a vacuum, slow lift, blot or squeegee wipe dryer and the like.

In the use of supports to which biopolymers such as polynucleotides are attached, an interrogation device often is used to examine the surface of a support for the presence and amount of signal after a reaction has taken place. The interrogation device may be a scanning device involving an optical system. In common optical analysis techniques, a tightly focused or pinpoint laser beam scans the surface of the support in order to excite labels such as fluorophores, which may be present on the surface of the support. For fluorescent label molecules, the laser beam excites the labels. Then, fluorescent emissions from the fluorophores are analyzed by means of an optical measuring device.

In a particular embodiment in accordance with the above, a device of the invention is inserted into a reader, such as a laser scanner, which has a suitable mounting means for receiving and releasably retaining the device in a known position. The scanner is able to read the location and intensity of signal such as fluorescence at each feature of an array following exposure to a fluorescently labeled sample such as a polynucleotide-containing sample. For example, such a scanner may be similar to the G2500A GeneArray Scanner available from Agilent Technologies, Inc., Palo Alto, Calif. Results from the interrogation can be processed such as by rejecting a reading for a feature which is below a predetermined threshold and/or forming conclusions based on the pattern read from the array such as whether or not a particular target sequence may have been present in the sample.

During reactions involving biopolymers it is often desired to heat the materials in contact with the surface of the support in the well of the present device. The heating of the support should be carried out in a manner that minimizes or avoids loss of liquid in the well of the device. This is particularly true where the liquid is sample, which is present in a relatively small quantity. Loss of liquid may occur by evaporation out of the device, or evaporation and condensation on the surface of the device, by wicking out of the well of the device and so forth. In one approach to address this potential problem, the present invention comprises an embodiment that is an apparatus for heating the surface of the support within the present device. The apparatus comprises at least one heating element above the support in the present device. The support is heated from the top by activation of the heating element so that there is a top to bottom temperature gradient. Usually, the gradient is sufficient enough to heat the support or the area adjacent the support or the liquid on the support without significant condensation. The temperature at which the support is heated is usually about 35 to about 75° C., more usually, about 45 to about 65° C. In another embodiment the support or the area adjacent the support is heated from above and below. In this approach the heating apparatus comprises two heating elements that are disposed above and below the support in the present device. The temperature achieved by the top heating element is higher than the temperature achieved by the bottom heating element. That is, the heating element above the support is activated with a higher level of energy to produce a higher temperature at such heating element than the heating element below the support. Both heating elements are adjusted to obtain the desired or predetermined temperature in or adjacent the liquid on the surface of the support. The temperature of the top heating element is usually about 0 to about 10° C., more usually, about 0.5 to about 5° C., higher than the temperature of the bottom heating element.

The heating element or heating elements in the above apparatus may be, for example, a flexible Kapton heater such as a Watlow K005020C5 heater, a heat exchanger with a heated fluid flowing through it, Peltier (thermoelectric) heater and the like. The manner in which energy is supplied to the heating element is dependent on the type of heating element, heat exchanger and so forth. For example, with a heating element, electrical power via wires or cables needs to be provided. With a heat exchanger, a heater, another heat exchanger and power, either from an electrical or fuel burning source, are employed to provide the heat necessary to heat the working fluid.

The heating apparatus in accordance with the present invention comprises a housing on the top of which, and in some embodiments on the bottom of which, is mounted a heater. The heating elements are mounted by means of thermal grease and Kapton tape, or double-sided Kapton tape, adhesive coated heater elements, thermal conductive epoxy, or a mechanical clamp, and the like. In one embodiment the housing comprises top and bottom portions that are designed to engage one another. The engagement may involve an interference fit, compression joint with thermal conduction gasket, screws around the perimeter, a toggle clamp, and so forth.

As mentioned above, during heating of liquids on the surface of the support, it may be desirable to have a cover over the chamber of the device to reduce or eliminate liquid loss. To this end the underside of the top portion of the heating apparatus may sealingly engage the top portion of the present device to provide an appropriate cover for the present device during the heating operation. In one approach the underside of the top part of the heating apparatus may comprise an O-ring, optionally and preferably, sequestered in part in a groove or recess around the underside of the top portion of the heating apparatus. When the top portion is brought into engagement with the bottom portion of the heating apparatus, the O-ring engages the top portion of the present device. Suitable means are employed to achieve the proper constriction of the O-ring so that a seal is formed that is sufficient to prevent or minimize liquid loss from the well of the present device. This may be accomplished by appropriate interference fitting of the top and bottom portions of the heating apparatus, manual or motorized toggle clamp, air cylinder, solenoid activated lever, and the like.

Figure 11:
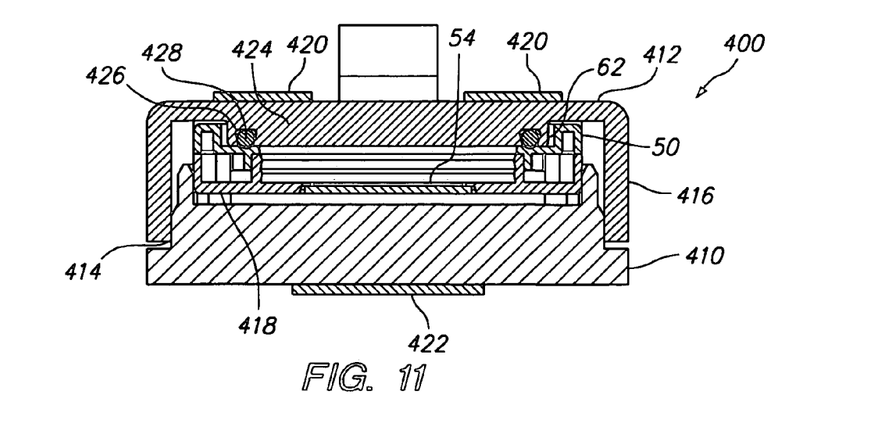
FIG. 11 is a diagrammatic sketch showing in cross-sectional perspective an embodiment of a heating apparatus for heating a device in accordance with the present invention.

An example of a heating apparatus in accordance with the present invention is depicted in FIG. 11. Referring to FIG. 11, heating apparatus 400 is shown. Apparatus 400 comprises a bottom portion 410 and a top portion 412. Bottom portion 410 comprises an indentation 414 around its perimeter. Top portion 412 comprises a downwardly depending wall 416, which is designed to engage in a mating fashion indentation 414 of bottom portion 410. The tolerances for indentation 414 and the inner surface of wall 416 are such as to create an interference fit for top portion 412 on bottom portion 410. Device 50 (FIG. 3) is seated within the interior of apparatus 400 on ledge 418 of bottom portion 410. Top portion 412 comprises heating element 420, which is shown positioned in top portion 412 so that it is centered or symmetrically placed over well 54 of device 50. Bottom portion 410 comprises heating element 422, which is shown positioned in bottom portion 410 so that it is centered under well 54 of device 50. The inner side of wall 424 of top portion 412 has recess 426 in which O-ring 428 is seated. The heating may be carried out in an automated fashion with the use of a computer to control the heating element and the temperature produced.

In the use of apparatus 400, device 50, with sample contained in well 54 thereof, is placed on ledge 418 of bottom portion 410. Top portion 412 is secured on bottom portion 410 by engaging wall 416 with indentation 414. When top portion 412 is fully seated on bottom portion 410, O-ring 428 compresses against surface 62 of device 50, thus forming a seal sufficient to prevent loss of vapor from well 54 and vapor from the device 400, during subsequent heating. Once top portion 412 and bottom portion 410 are engaged, heating element 420 and heating element 422 are activated to bring the liquid within well 54 to the desired predetermined temperature. Following the heating process, top portion 412 is disengaged from bottom portion 410 and device 50 is removed from its position within bottom portion 410 and moved to an area for subsequent processing such as liquid removal, washing, drying and the like. A noteworthy feature of this aspect of the present invention is that the above procedure may be partially or fully automated. A completely automated process may be carried out in a single chamber.

As mentioned above, processing of the samples may include mixing fluid reagents and wash solutions with the samples on the surface of the supports. Mixing may be accomplished in a number of ways. For example, mixing may be accomplished mechanically by agitation such as that achieved by (i) gross mechanical motion of the device, for example, rocking, rotating, tilting, orbiting, etc., (ii) vortex mixing through the action of directional gas or fluid flow guided by directional nozzles, (iii) fluid motion through the action of recirculated fluid pumping, (iv) ultrasonically by bulk-material or surface acoustic waves, (v) locally induced bubble formation and deformation through the action of localized heating, (vi) providing constant or intermittent dispensing and removal of wash fluid, and so forth.

The reagents and wash solutions are usually in an aqueous medium. The aqueous medium may contain buffering agents such as, e.g., borate, phosphate, carbonate, Tris, barbital and the like at pH of about 3 to about 11 and/or polar cosolvents such as oxygenated organic solvents of from 1–6, more usually from 1–4, carbon atoms, including dimethylsulfoxide, alcohols, ethers, formamide, urea, and the like.

One aspect of the present invention then includes methods for mixing materials on the surface of a support. At least one reagent is placed in the well of the present device on the surface of the support. Usually, the surface has at least a residual amount of a sample thereon because usually the means of removal of sample does not remove all molecules of the sample on the surface. After introduction of the at least one reagent, a stream of gas is directed at the surface of the support, i.e., the liquid on the surface of the support. The pressure of the stream and the angle of its delivery create a vortex in the liquid on the surface of the support sufficient to mix the residual sample and the reagent. In general, the gas is air although other gases may be employed as long as such gases are inert to the reactions occurring on the surface of the support, to the reagents employed, sample, hybridization buffer and so forth. The gas used may be, for example, an inert gas such as, e.g., nitrogen, argon, neon, helium and the like. The gas is normally delivered by means of a nozzle adapted to deliver a stream of gas. The pressure of the gas can be relatively low such as, for example, about 1 to about 3 psig. Accordingly, the nozzle is connected to a suitable pump or laboratory air or nitrogen supply and regulated to the proper pressure. For this purpose an air compressor with filter and regulator or gas supply and the like may be employed. The angle of delivery of the gas is often a factor of the slope of the walls of the housing of the present device. The angle of delivery is usually about −1 to about −35 degrees from horizontal, more usually, about −3 to about −20 degrees. To this end the nozzle is typically mounted and oriented to provide the desired angle of delivery of the gas stream into the device of the invention.

Figure 12:
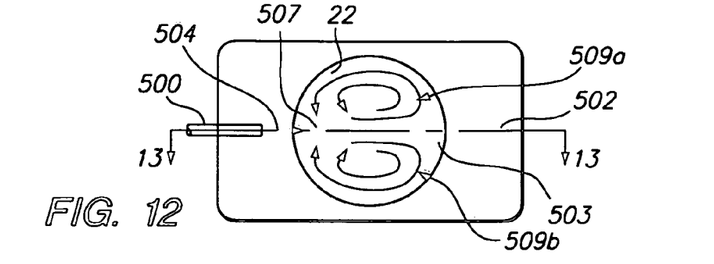
FIG. 12 is a diagrammatic sketch depicting a top view of a vortex pattern induced in a liquid on a support in a device in accordance with the present invention by application of a gas stream.
Figure 13:
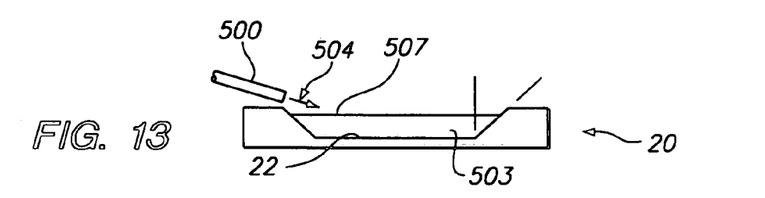
FIG. 13 is a cross-sectional view of the sketch of FIG. 12 taken along lines 13—13.

The pattern of vortex mixing is dependent on the point at which the gas stream impinges the liquid in the well of the present device. The stream may be directed at a centerline of the surface of the support at a point that is about 1 to about 10 mm from the edge of the well's wall. In this way a substantially symmetrical vortex pattern results that is essentially semi-circular on each side of the centerline. This may be seen more clearly with reference to FIGS. 12–13. Nozzle 500 is directed at the centerline 502 of liquid 503 on the surface of support 22 of device 20 (FIG. 1). The point of application 507 of gas stream 504 along centerline 502 is about 1 to about 5 mm, usually about 2 mm, from the edge of the well's wall along centerline 502. In this way a symmetrical vortex patterns 509a and 509b are obtained that provides for mixing of liquid 503 on the surface of support 22. The symmetrical vortex patterns are semi-circular.

Figure 14:
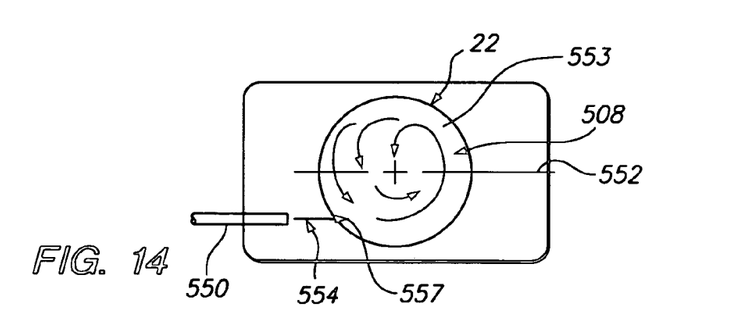
FIG. 14 is a diagrammatic sketch depicting a top view of another vortex pattern induced in a liquid on a support in a device in accordance with the present invention by application of a gas stream.

Alternatively, the stream of gas may be directed at a point that is offset from a centerline of the surface of the support. The offset may be any point that is between the centerline and the edge of the well of the present device. Usually, the offset is from one quarter (¼) to three-eighths (⅜) of the diameter or width of the well. An example of this aspect of the present invention is depicted in FIG. 14. Nozzle 550 is directed at a point 554 that is displaced from centerline 552 of liquid 553 on the surface of support 22 of device 20 (FIG. 1). Point 557 of application of gas stream 554 is offset about ⅜ of the diameter or width from centerline 552. In this way a vortex pattern 508 is obtained that provides for mixing of the liquid on the surface of support 22. Vortex pattern 508 is essentially circular in the embodiment shown.

Depending on the point of application of the gas stream, a number of other vortex patterns is possible. In essence, the present invention permits a predetermined pattern of mixing to be achieved by adjusting the parameters of the gas stream such as pressure, angle of delivery, point of application, angle of deflection of the nozzle, number of nozzles, and so forth. The basic idea is to transfer momentum from the gas stream to the buffer or wash solution in the well of the device. To this end, the proper values of the above mentioned variables must be set. With regards to the pressure, if it is set too high, the buffer/wash solution may splash out of the well of the device. If the pressure is too low, then the gas stream will not have the proper momentum to transfer to the wash/buffer solution. If the angle of delivery is too shallow, then no momentum transfer will occur, too high and splashing will occur. If the point of application is incorrect, then the vortex mixing will not occur and so forth.

The gas stream may be applied in an oscillating mode. The level of oscillation is usually about 0.5 to about 10 Hz, more usually, about 1 to about 3 Hz. Oscillation may be achieved by moving the nozzle distributing the gas stream with respect to the liquid, moving the liquid with respect to the nozzle, or combinations thereof. Preferably, the liquid is held stationary and the nozzle is moved to create the desired level of oscillation. The gas stream may be oscillated from the centerline to an edge of the surface on which the liquid is contained. Preferably, the gas stream is oscillated about the centerline. It should be noted that in the device of the invention the housing is open. Thus, in the above operation or in any operation involving the device, it is important that the device be oriented with respect to gravity so that liquid does not spill out of the device and preferably does not spill, or wick, out of the well of the device.

As mentioned briefly above, the mixing of liquids on the surface of a support in the well of a device of the invention may also be accomplished by subjecting the device to motion sufficient to mix the liquids in the well. The liquids may be residual sample and the at least one reagent such as, for example, a wash buffer. The motion may be orbital or linear. The intensity of the motion is that sufficient to mix the liquids on the surface. Such intensity is a function of the velocity of the liquid in the well of the device. The linear velocity shall range from about 0.14 inches per second (about 3.35 mm per second) to about 0.82 inches per second (about 20.7 mm per second). The orbital frequency shall range from about 0.33 to about 0.2 Hz.

One embodiment of the present invention comprises mixing materials on the surface of a support where the surface of the support has at least a residual amount of a sample thereon and is substantially free from an evaporation layer. In known approaches an evaporation layer such as a film of mineral oil is employed to reduce the evaporation of liquid on the surface of a support. The use of such a layer is disadvantageous because it will interfere with the chemistry of the wash buffer and the surface chemistry of the support. In the present invention, an evaporation layer is not necessary.

The present invention includes a method for carrying out a binding reaction. A sample suspected to contain an analyte or component of interest such as a biopolymer is introduced onto the surface of a support of a device in accordance with the present invention. The sample is incubated on the support for a time and under conditions of temperature and the like sufficient to permit binding reactions to occur between components of the sample and complementary binding members on the surface of the support. Such samples include biological fluids such as blood, serum, plasma, sputum, lymphatic fluid, semen, vaginal mucus, feces, urine, spinal fluid, and the like; biological tissue such as tissue biopsies, hair and skin; and so forth. Other samples include cultures of mammalian and non mammalian cells, microorganisms, viruses, yeast, fungi, and the like, plants, insects, aquatic organisms, food, forensic samples such as paper, fabrics and scrapings, water, sewage, medicinals, etc. When necessary, the sample may be pretreated with reagents to liquefy the sample and release components of interest such as nucleic acids from binding substances. Such pretreatments are well known in the art.

After the appropriate period of incubation, the sample is removed from the surface. This may be accomplished by aspiration, air knife, and so forth as discussed above. Usually, a residual amount of the sample remains on the surface, which is contacted with a wash solution such as a buffered aqueous solution. The amount of wash solution is usually about 10 to about 100 times the amount of sample that was initially employed. A stream of gas is directed at the surface of the support. The pressure of the stream and the angle of the stream create a vortex on the surface sufficient to mix the sample and the wash solution as discussed above. The wash solution is removed from the surface by aspiration, air knife or other means as discussed above. Usually, the surface of the support is dried. Drying may be accomplished by means of an air knife, spin dryer, by slowly (about 0.5 to about 2, usually about 1, mm per second) lifting the supports out of the last wash buffer so that the buffer solution is stripped from the supports, and so forth. It should be noted that the wash buffer may or may not contain a surfactant when this step is performed.

The aforementioned method has particular application to the detection of the presence of a target polynucleotide in a sample. The method is carried out as discussed above. Then, the washed surface is examined for the presence of a binding reaction between the polynucleotides thereon and the target polynucleotide. The presence of such binding reactions indicates the presence of the target polynucleotide in the sample. Detection may be carried out using techniques as discussed above.

In using the devices in accordance with the present invention it is often the case that multiple devices are employed to detect one or more analytes in a sample. Accordingly, samples may be introduced, respectively, into the wells of multiple devices, which then are subjected in groups to conditions for achieving the desired binding reactions if the appropriate analytes are present in the sample. To this end the devices may be placed in a suitable holding apparatus designed to accommodate a plurality of devices in accordance with the present invention. The holding apparatus may be moved to various stations for conducting reactions and washing operations. The above processes may be automated. The holding apparatus may be a circular tray such as a carousel, a linear tray and so forth.

To assist in the identification and indexing functions where a plurality of devices in accordance with the present invention are employed, the housing of the device may comprise an identification code such as a bar code and the like. The identification code is usually placed in a location that does not interfere with the processing of the samples on the supports in the devices of the invention. The identification code may be placed on the outside of the housing of the device. A suitable reading device is employed for reading the identification code. In this way the identity and location of each of the devices of the invention can be tracked. Such information may be loaded into a database for storage of the data.

The results from the analysis involving exposing the support to the sample may optionally be processed. In this regard the results obtained from the aforementioned examining of the support may be processed by, for example, computer aided data analysis. In addition, the results may be forwarded to a remote location. By the term "remote location" is meant a location that is physically different than that at which the results are obtained. Accordingly, the results may be sent to a different room, a different building, a different part of city, a different city, and so forth. Usually, the remote location is at least about one mile, usually, at least ten miles, more usually about a hundred miles, or more from the location at which the results are obtained. The method may further comprise transmitting data representing the results. The data may be transmitted by standard means such as, e.g., facsimile, mail, overnight delivery, e-mail, voice mail, and the like.

As mentioned above, methods of using the devices of the invention may be automated. In such a situation, the methods may be carried out under computer control, that is, with one or more embedded computers and an optional external supervisory computer. The embedded computers may be microprocessor- or microcontroller-type, configured with internal central processing units, program and data memory, analog-to-digital and digital-to-analog conversion interfaces, digital input and output (I/O) interfaces, suitable for the control tasks required. These embedded computers are driven by custom embedded software specific to the control tasks and operation actions and methods described herein. The software programs provide for various steps involved in using the devices of the invention. Such software may be written, preferably, in Visual BASIC, Visual C$^{++}$ or in processor-specific assembly language.

The external supervisory computer may, for example, be an IBM® compatible personal computer (PC). Supervisory computer software, that may be used to carry out the methods herein, may use C/C$^{++}$, Visual BASIC, Visual C$^{++}$, suitably extended via user-written functions and templates.

It should be understood that the above computer information and the software used herein are by way of example and not limitation. The present methods may be adapted to other embedded and supervisory computers, operating systems and runtime application-specific software.

EXAMPLES

The invention is demonstrated further by the following illustrative examples. Parts and percentages are by weight unless indicated otherwise. Temperatures are in degrees centigrade (° C.).

In-situ synthesized 25-mer oligonucleotide arrays containing 8455 features were fabricated according to standard molecular array preparation techniques on 1-mm thick glass and diced to 22×22-mm die. Each die was then assembled into a device in accordance with the present invention using techniques discussed above. The arrays contained 4×-replicated, optimized probes against human reference sequence genes (RefSeq). Three sequences were used per gene, for a total of 12 probes per gene. The array included a variety of positive and negative control probes. The probes were arranged into 4 identical quadrants on the die.

A fluorescently labeled mRNA sample from K562 cells was injected into each packaged array. The sample quantity was 250 $\mu$L. The packaged arrays were hybridized by incubation overnight at 60° C. During incubation, the contents of the packaged arrays were bubble mixed by package rotation.

At the end of the hybridization period, the packaged arrays were removed from the incubator and cooled for prescribed times (1–10 minutes) simply by being exposed to room temperature conditions. Each support was washed using several different protocols, each involving multiple washings with buffer (0.9M Sodium Chloride and 0.09M Sodium Citrate, available from Amresco, Solon, Ohio and 0.015M Sodium Chloride and 0.0015M Sodium Citrate, available from Amresco).

After the wash protocols were completed, the supports were dried by centrifugal action in a spin dryer (1800 rpm for 60 seconds). The devices were then moved to a scanner where the arrays were scanned for fluorescent signal and the results were processed.

All publications, patents and patent applications cited in this specification are herein incorporated by reference as if each individual publication, patent or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible, in view of the above teachings. The embodiments were chosen and described in order to explain the principles of the invention and its practical applications and to thereby enable others skilled in the art to utilize the invention.

What is claimed is:

1. A device comprising:
   (a) a housing and
   (b) a non-porous support in a well of said housing wherein a surface of said support comprises an array of biopolymers, said well having walls and said housing comprising at least one wall extending from an area adjacent a top edge of said well to a top portion of said housing, wherein a ledge extends horizontally from said top edge of said well to an area adjacent a bottom edge of said at least one wall.

2. A device according to claim 1 wherein said at least one wall is designed such that corners thereof are radiused.

3. A device according to claim 1 wherein said at least one wall is at least partially sloped in an area thereof adjacent said well.

4. A device according to claim 3 wherein said at least one wall is at least partially sloped at about 10 to about 60 degrees.

5. A device according to claim 3 wherein said ledge extends from an edge of said well to the sloping portion of said at least one wall.

6. A device according to claim 3 wherein said at least one wall is fully sloped from said ledge to the top portion of said housing.

7. A device according to claim 3 wherein said partially sloped wall is sloped at least about 35 degrees.

8. A device according to claim 3 wherein said at least partially sloped wall is sloped at about 30 to about 55 degrees.

9. A device according to claim 3 wherein the slope of said partially sloped wall is constant.

10. A device according to claim 3 wherein the slope of said partially sloped wall is not constant.

11. A device according to claim 1 wherein the height of said walls of said well is at least about 0.010 inches.

12. A device according to claim 1 wherein a width of said ledge is about 0.050 to about 1.00 inches.

13. A device according to claim 12 wherein said at least one wall comprises a partially sloped portion in an area adjacent said ledge and a vertical portion extending from said partially sloped portion to a top portion of said device.

14. A device according to claim 1 wherein said ledge is rectangular in shape about said well.

15. A device according to claim 1 wherein said ledge is circular in shape about said well.

16. A device according to claim 15 wherein said at least one wall is a circular wall extending from said ledge to a top portion of said device.

17. A device according to claim 1 wherein said at least one wall is a circular wall extending from said ledge to a top portion of said device.

18. A device according to claim 1 wherein said device comprises at least two walls that are fully sloped from said ledge to a top portion of said device.

19. A device according to claim 18 wherein said device comprises two opposing walls that are fully sloped from said ledge to the top portion of said device and two opposing walls extending vertically from said ledge to said top portion.

20. A device according to claim 18 wherein said device comprises four walls that are fully sloped from said ledge to the top portion of said device.

21. A device according to claim 1 wherein said ledge comprises a polished surface that prevents wicking of a liquid along said ledge.

22. A device according to claim 1 wherein said biopolymers are polynucleotides.

23. A device according to claim 22 wherein said polynucleotides are DNA.

24. A device according to claim 22 wherein said biopolymers are proteins or peptides.

25. A device according to claim 1 comprising a single well and further comprising a cover.

26. A device according to claim 1 wherein said at least one wall is designed such that any corners thereof are distant from the edge of said well by about 0.1 inch to about 1 inch.

27. A device according to claim 1 wherein said support has dimensions of about 0.5 inches to about 1.5 inches by about 0.5 inches to about 1.5 inches or by about 2.0 inches to about 4.0 inches with a thickness of about 0.030 to about 0.05 inches.

28. A device comprising:
    (a) a housing and
    (b) a support in a well of said housing, wherein a surface of said support comprises a plurality of biopolymers, said well having walls and said housing comprising at least one wall extending upwardly from a top edge of said well to a top portion of said housing, wherein said at least one wall is at least partially sloped in an area thereof adjacent said well and wherein the slope of said partially sloped wall is not constant.

29. A device comprising:
    (a) a housing and
    (b) a support in a well of said housing wherein a surface of said support comprises an array of biopolymers, said well having walls and said housing comprising at least one wall extending from an area adjacent a top edge of said well to a top portion of said housing, wherein a ledge extends horizontally from said top edge of said well to an area adjacent a bottom edge of said at least one wall and wherein said at least one wall comprises a partially sloped portion in an area adjacent said ledge and a vertical portion extending from said partially sloped portion to a top portion of said device.

30. A device comprising:
    (a) a housing and
    (b) a support in a well of said housing wherein a surface of said support comprises an array of biopolymers, said well having walls and said housing comprising at least one wall extending from an area adjacent a top edge of said well to a top portion of said housing, wherein a ledge extends horizontally from said top edge of said well to an area adjacent a bottom edge of said at least one wall and wherein said device comprises at least two walls that are fully sloped from said ledge to a top portion of said device and wherein said device comprises two opposing walls that are fully sloped from said ledge to the top portion of said device and two opposing walls extending vertically from said ledge to said top portion.

31. A device comprising:
    (a) a housing and
    (b) a support in a well of said housing wherein a surface of said support comprises an array of biopolymers, said well having walls and said housing comprising at least one wall extending from an area adjacent a top edge of said well to a top portion of said housing, wherein a ledge extends horizontally from said top edge of said well to an area adjacent a bottom edge of said at least one wall and wherein said at least one wall is at least partially sloped in an area thereof adjacent said well and wherein the slope of said partially sloped wall is not constant.

* * * * *